US00PP10647P

United States Patent [19]

DeLeon

[11] Patent Number: Plant 10,647

[45] Date of Patent: Oct. 13, 1998

[54] AECHMEA PLANT NAMED 'SUPERB'

[75] Inventor: Nat DeLeon, Goulds, Fla.

[73] Assignee: DeLeon's Bromeliads Inc., Goulds, Fla.

[21] Appl. No.: 796,265

[22] Filed: Feb. 6, 1997

[51] Int. Cl.[6] ..... A01H 5/00

[52] U.S. Cl. ..... Plt./88.8

[58] Field of Search ..... Plt./88.8

*Primary Examiner*—Elizabeth C. Kemmerer
*Attorney, Agent, or Firm*—Burns, Doane, Swecker & Mathis, L.L.P.

[57] ABSTRACT

A new and distinct variety of *Aechmea fasciata* is provided which forms a large abundantly branched pink-bracted inflorescence with contrasting blue flowers. The leaves are dark green, wide and spineless and are mottled with silver-white (as illustrated). The new variety can be readily distinguished from the 'DeLeon' variety (U.S. Plant Pat. No. 7,832) by a taller and more rapid growth habit, more abundant branching, wider leaves, and the presence of the mottled leaf pattern that can be contrasted with the silver-white bands and barring on the leaves of the 'DeLeon' variety.

3 Drawing Sheets

SUMMARY OF THE INVENTION

Aechmea plants are known to comprise a genus of over 168 species of evergreen perennials suitable for cultivation in the home or under glass. Aechmea may be terrestrial or epiphytic. For the most part the plants of the species vary in diameter from 12 to 18 inches to 3 or 4 feet and have rosettes of spiny edged leaves.

The flowers and bracts of Aechmea frequently have brilliant colors and may last up to several months. The range of colors for Aechmea is generally from yellow through orange but may also include pink, orange, red and red-purple. Tubular, three-petalled flowers may also appear but are usually short lived.

Aechmea may be advantageously grown as pot plants for greenhouse or home use. Typically the plants are shaded from direct sunlight and the central vase-like part of the leaf rosette is normally filled with water.

Aechmea is native to tropical America. Leaves of the Aechmea are usually formed as basal rosettes which are stiff and entire and in several vertical ranks. Aechmea have terminal spikes or panicles which are often bracted with the petals united in a tube that is longer than the calyx.

The new variety of *Aechmea fasciata* of the present invention was created during August 1990, at Miami, Fla. by artificial pollination wherein two parents were crossed which previously had been studied in the hope that they would contribute the desired characteristics.

The female parent (i.e., seed parent) was an unnamed *Aechmea fasciata* clone designated No. 79 (non-patented in the United States), and the male parent (i.e., pollen parent) was an unnamed *Aechmea fasciata* clone designated No. 92 (non-patented in the United States).

The seeds resulting from the above pollination were sown and small plants were obtained which were physically and biologically different from each other. Selective study during August 1992 resulted in the identification of a single plant of the new variety.

It was found that the new variety of the present invention possesses the following combination of characteristics:

(a) forms a large pink-bracted inflorescence with contrasting blue flowers that is abundantly branched.
(b) forms wide dark green spineless leaves that are mottled with silver-white, and (c) exhibits a vigorous tall growth habit.

The new variety of the present invention can be readily distinguished from the *Aechmea fasciata* 'DeLeon' variety (U.S. Plant Pat. No. 7,832). More specifically, the new variety forms an inflorescence that is taller and more abundantly branched, forms wider leaves, forms a silver-white mottled leaf pattern that can be contrasted to the silver-white bands or barring on the leaves of the 'DeLeon' variety, and grows faster than the 'DeLeon' variety.

The new variety has been carefully evaluated and has been found to undergo asexual propagation at Goulds, Fla. beginning in October, 1992. More specifically, asexual propagation by the cutting of off-shoots growing from the base of the plant has shown that the characteristics of the new variety are stable and are strictly transmissible from one generation to another.

The new variety of the present invention has been named the 'Superb' variety.

The new 'Superb' variety has not been observed and tested under all possible environmental conditions to date. Accordingly, the phenotype may vary with variations in environmental conditions, such as temperature, light intensity, day length, humidity, etc., without any change in the genotype.

BRIEF DESCRIPTION OF THE PHOTOGRAPH

The accompanying photographs show as nearly true as it is reasonably possible to make the same in color illustrations of this character, a typical specimen of the plant and the foliage of the new variety. The plant was grown in a greenhouse at Goulds, Fla., while using growing conditions that are standard for the industry.

FIG. 1 illustrates the original plant of the new variety after 18 months of growth when finished in a 15 cm pot.

FIG. 2 illustrates a closer view of the infloresence and leaves of the new variety. The attractive pink brachts are shown.

FIG. 3 illustrates for comparative purposes the upper leaf surface of the new variety on the right, and the upper leaf surface of the 'DeLeon' variety (U.S. Plant Pat. No. 7,832) on the left.

DETAILED DESCRIPTION

The chart used in the identification of colors is that of The Royal Horticultural Society (R.H.S. Colour Chart). The description is based upon the observation of the plant of FIG. 1 when grown at Goulds, Fla. under greenhouse conditions that are standard for the industry.

Classification: *Aechmea fasciata,* cv. 'Superb'.

Plant:

*Growth habit.*—Basal rosettes of strap-like leaves arranged around a central axis.

*Height.*—Approximately 52 cm. including inflorescence.

*Diameter.*—Approximately 50 to 78 cm.

Foliage:

*Leaf size.*—The basal leaves are approximately 25 to 39 cm. in length, and approximately 10 to 12 cm. in width.

*Leaf shape.*—The leaf blade is ligulate with a broadly rounded apiculate apex, slightly channeled, and the margins are entire and spineless.

*Leaf sheath.*—Broadly elliptic, approximately 7 to 12 cm. in length, and approximately 6 to 12 cm. in width.

*Leaf texture.*—The leaf blade is thick, coriaceous, and with dense silver-white lepidote concentrated in bands and spots. Markings are particularly dense on the abaxial surface of the leaf.

*Leaf color.*—The adaxial and abaxial surfaces are near Green Group 137A, but tend to be somewhat darker and greener.

*Number of leaves.*—The plant commonly produces approximately 17 leaves before producing an inflorescence.

*Roots.*—Wiry with fine laterals, and yellow-green changing to brown in coloration.

Bracts:

*Primary bracts.*—The primary bracts number approximately 23, are thin and papery, posses a surface that is densely appressed lepidote, possess a margin that is entire and nearly spineless, and are located at the base of each branch spike. The length is approximately 6 to 10 cm. and the width is approximately 1.8 to 2.5 cm., and the shape is lanceolate to triangular with an acute tip. The adaxial and abaxial surfaces are near Red Group 55C in coloration.

*Floral bracts.*—The floral bracts underlying the flowers are coriaceous, process a surface that is pale appressed lepidote, possess a margin that is entire and nearly spineless, commonly number approximately 190, are approximately 2.8 to 3.3 cm. in length and approximately 1.2 to 1.5 cm. in width, and possess a triangular shape with an acute to attenuate tip. The adaxial and abaxial surfaces are near Red Group 54B in coloration.

*Scape bracts.*—The scape bracts are thin and papery, possess a surface that is densely appressed lepidote, possess a margin that is entire and nearly spineless, encircle the scape, number approximately 6, are approximately 8 to 12 cm. in length and approximately 2.5 to 2.8 cm. in width, and posses a shape that is lanceolate with an acute to acuminate tip. The adaxial and abaxial surfaces are near Red Group 56A in coloration.

*Scape.*—The surface is densely covered with white floccose, the height is approximately 33 cm., the diameter is approximately 2 cm., and the color is near Red Group 53C.

*Branch spikes.*—The branches are sessile and are positioned at about 45° with respect to the main axis. The branches commonly extend up to approximately 5 cm. in length, and approximately 20 branch spikes commonly are present. Approximately 7 to 12 buds/flowers commonly are present on each branch spike.

*Shape of inflorescence.*—Densely digitate, pyramidal in configuration, commonly approximately 12 cm. in height, and commonly approximately 22 cm. in width.

Flowers:

*Calyx.*—Three sepals are present, approximately 10 to 11 mm. in length, and near Red Group 55D in coloration.

*Corolla.*—Tubular, three ligulate petals are present, approximately 24 to 28 mm. in length, and Blue Group 102D fading to Red-Purple Group 57C to black in coloration.

*Time of Blooming.*—The flowering of mature plants commonly begins approximately 14 weeks after induction during the warm summer months, and approximately 16 to 17 weeks after induction during the cool winter months.

*Duration of Inflorescence.*—The inflorescence commonly will hold its color approximately 3 to 4 months during the warm summer months, and approximately 4 to 6 months during the cool winter months.

Floral organs:

*Ovary.*—Inferior, possesses three locules, approximately 6 mm. in length, and white in coloration.

*Anthers.*—Approximately 5 mm. in length, and white in coloration.

Seed characteristics: Typical of the *Aechmea fasciata* species.

I claim:

1. A new and distinct variety of *Aechmea fasciata* plant characterized by the following combination of characteristics:

(a) forms a large pink-bracted inflorescence with contrasting blue flowers that is abundantly branched,
(b) forms wide dark green spineless leaves that are mottled with silver-white, and
(c) exhibits a vigorous tall growth habit;

substantially as herein illustrated and described.

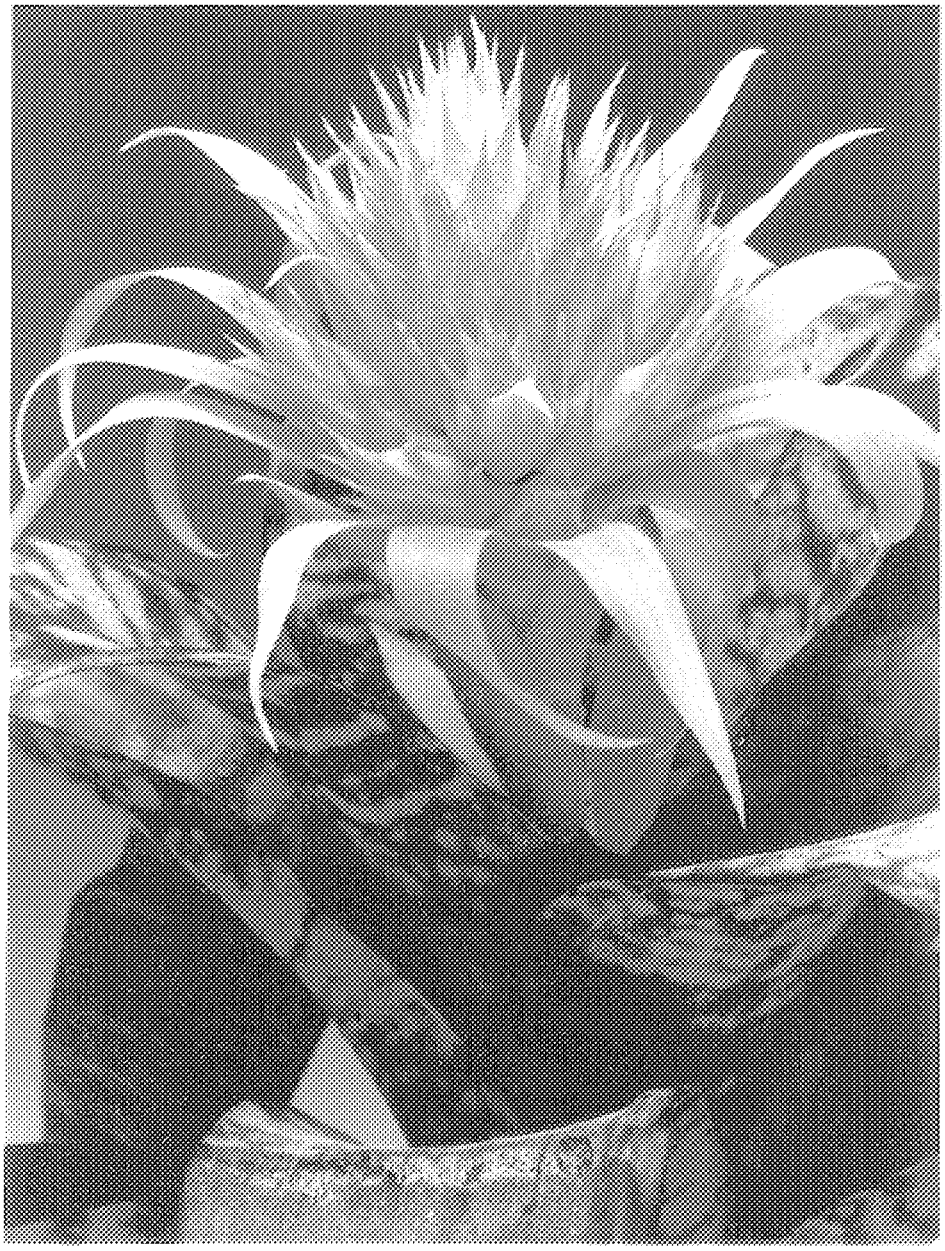

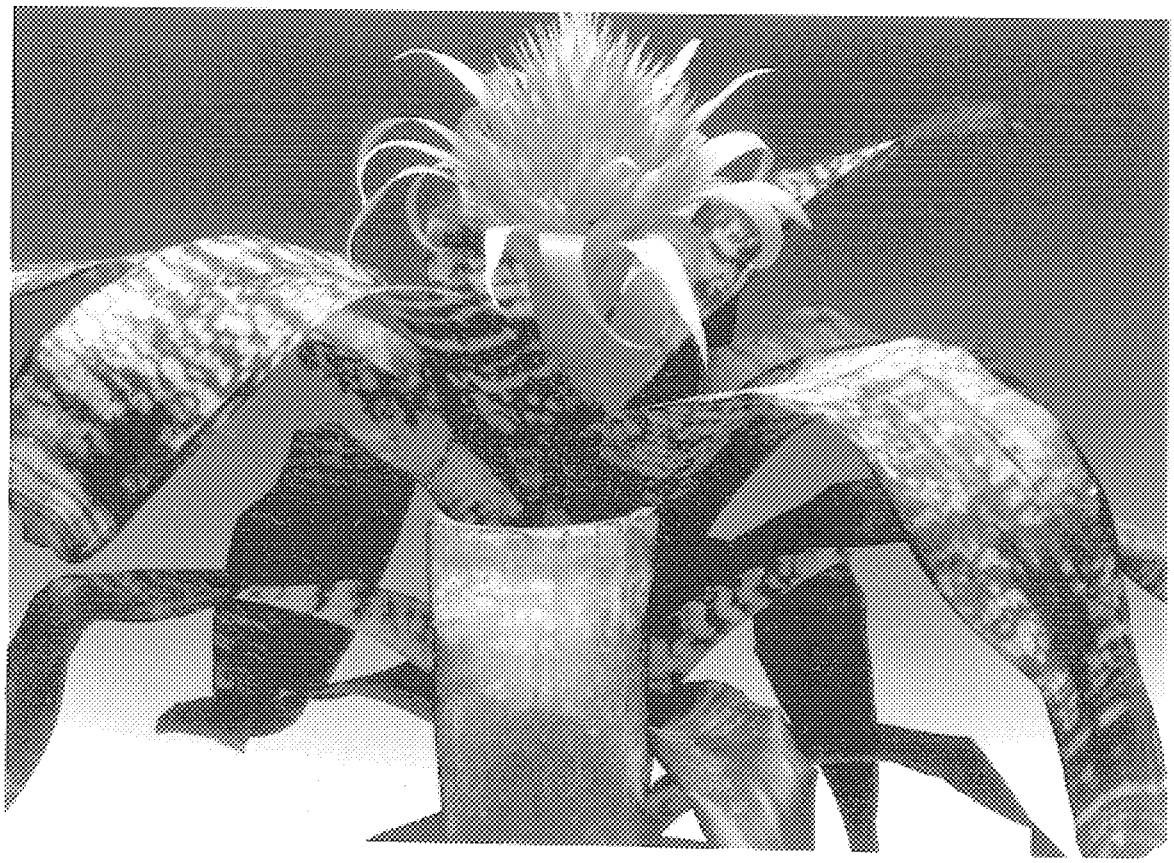

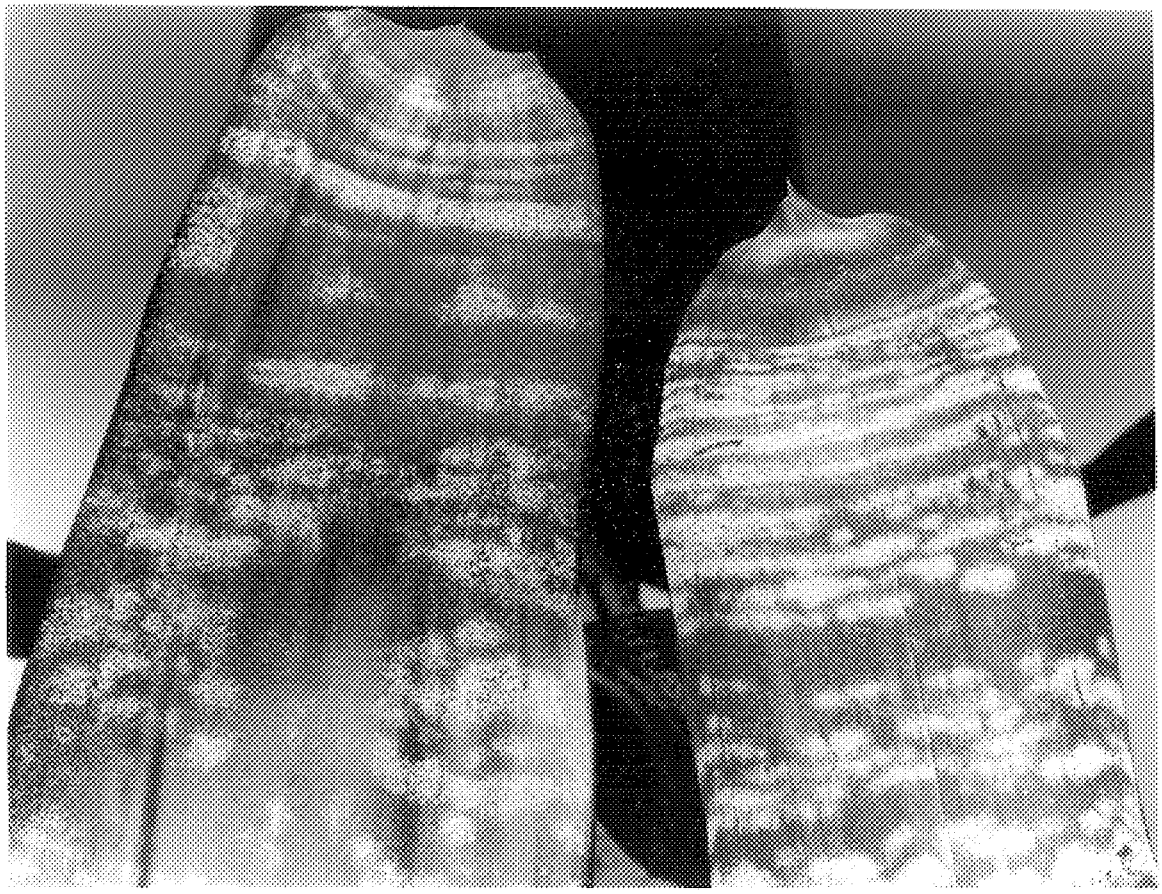

* * * * *